United States Patent [19]

Spada et al.

[11] Patent Number: 4,866,074
[45] Date of Patent: Sep. 12, 1989

[54] NAPHTHERIDINONE- AND PYRIDOOXAZINONE-PYRIDONE COMPOUNDS, CARDIOTONIC COMPOSITIONS INCLUDING SAME, AND THEIR USES

[75] Inventors: Alfred P. Spada, Ambler; William L. Studt, Harleysville; Henry F. Campbell, North Wales; Donald E. Kuhla, Doylestown; Thomas Tucker, North Wales, all of Pa.

[73] Assignee: Rorer Pharmaceutical Corporation, Fort Washington, Pa.

[21] Appl. No.: 255,728

[22] Filed: Oct. 11, 1988

Related U.S. Application Data

[63] Continuation-in-part of Ser. No. 47,394, May 8, 1987, Pat. No. 4,822,794.

[51] Int. Cl.[4] .................. A61K 31/435; C07D 498/04

[52] U.S. Cl. .................. 514/300; 514/302; 546/113; 546/116

[58] Field of Search ............... 546/113, 116; 514/300, 514/302

[56] References Cited

U.S. PATENT DOCUMENTS

| | | | |
|---|---|---|---|
| 3,853,880 | 12/1974 | Challier et al. | 546/113 X |
| 3,984,405 | 10/1976 | Krapcho | 544/105 |
| 4,119,631 | 10/1978 | Gottschlich et al. | 546/116 X |

*Primary Examiner*—Richard L. Raymond

[57] ABSTRACT

This invention relates to substituted pyridooxazinone and naphtheridone pyridones which are useful as cardiotonic agents for the treatment of congestive heart failure, to methods for increasing cardiac contractility using said compounds, and pharmaceutical compositions including the same.

11 Claims, No Drawings

NAPHTHERIDINONE- AND PYRIDOOXAZINONE-PYRIDONE COMPOUNDS, CARDIOTONIC COMPOSITIONS INCLUDING SAME, AND THEIR USES

This is a continuation-in-part of U.S. Ser. No. 47,394, filed May 8, 1987, now U.S. Pat. No. 4,822,794, and PCT/US88/01504 filed May 4, 1988.

FIELD OF INVENTION

This invention relates to diazabicyclic substituted pyridones which are useful as cardiotonic agents for the treatment of congestive heart failure. This invention also relates to methods for increasing cardiac contractility using said compounds, and pharmaceutical compositions including said compounds.

Congestive heart failure is a life-threatening condition in which myocardial contractility is depressed so that the heart is unable to adequately pump the blood returning to it. Normal pathologic sequelae include decreased cardiac output, venous pooling, increased venous pressure, edema, increased heart size, increased myocardial wall tension, and eventually cessation of contractility.

REPORTED DEVELOPMENTS

Drugs which increase the tone of the heart muscle are described as having positive inotropic activity and are characterized as cardiotonic agents. Digitalis glycosides have long been used to increase myocardial contractility and reverse the detrimental changes seen in congestive heart failure. More recently, dopamine, dobutamine, and amrinone have been used to provide necessary inotropic support for the failing heart.

Cardiotonic agents which are described as having positive inotropic activity include the 5-pyridyl substituted pyridones disclosed in U.S. Pat. Nos.: 4,004,012; 4,072,746; 4,107,315; 4,137,233; 4,199,586 and 4,271,168; in GB No. 2070606A; and in PCT published Appl. No. PCT/CH81/00023. Other cardiotonic drugs include the diazacyclic substituted carbostyril compounds disclosed in U.S. Pat. Nos. 4,414,390 and 4,415,572, cardiotonic pyridyl substituted carbostyril compounds disclosed in EPO application Serial No. 84308925.1, and cardiotonic 5-substituted-1,6-naphthyridine-2(1H)-one compounds disclosed in U.S. Pat. No. 4,657,915.

Cardiotonic bicyclic heteroaryl-5-substituted pyridyl compounds are disclosed in PCT published application Serial Nos. PCT/US83/01285 and PCT/US87/01489 (WO 88/00188); and, cardiotonic diazheterocyclic-5-substituted pyridyl compounds are disclosed in U.S. Pat. Nos. 4,432,979, 4,514,400 and 4,539,321. Each of the aforementioned is assigned to the same assignee as the present application.

SUMMARY OF THE INVENTION

The present invention relates to naphtheridone- and pyridooxazinone-pyridone compounds which are useful for increasing cardiac contractility in humans and other mammals.

The compounds of the present invention include compounds of Formula I:

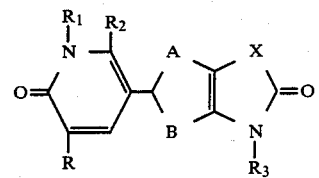

wherein:
A is —C= or —N=;
B is —C=C—, —C=N— or —N=C—; provided that A or B represents a nitrogen-containing group;
X is —$(CR_4R_5)_a$—$(O)_b$—$(CR_6R_7)_c$—;
a and c are 0, 1 or 2;
b is 0 or 1;
provided that a+b+c=1, 2 or 3;
R is hydrogen, alkyl, alkoxyalkyl, hydroxyalkyl, nitro, halo, cyano, carbamoyl, alkyl carbamoyl, formyl, aminoalkylene or amino; $R_1$, $R_2$, $R_3$, $R_5$, $R_6$ and $R_7$ are hydrogen, alkyl, or aralkyl; $R_4$ is hydrogen, alkyl, aryl, or aralkyl;
geminal $R_6$ and $R_7$ groups may together form a spiro substituent, —$(CH_2)_d$—, where d is 2 to 5; and pharmaceutically acceptable salts thereof.

This invention relates also to methods for increasing cardiac contractility using pharmaceutical compositions including an effective inotropic amount of a compound of Formula I above.

DETAILED DESCRIPTION

As employed above and throughout the disclosure, the following terms, unless otherwise indicated, shall be understood to have the following meanings:

"Alkyl" means a saturated aliphatic hydrocarbon which may be either straight or branched-chained containing from about 1 to about 6 carbon atoms.

"Lower alkyl" means an alkyl group as above, having 1 to about 4 carbon atoms.

"Aralkyl" means an alkyl group substituted by an aryl radical where aryl means a phenyl or phenyl substituted with one or more substituents which may be alkyl, alkoxy, amino, nitro, carboxy, carboalkoxy, cyano, alkyl amino, halo, hydroxy, hydroxyalkyl, mercaptyl, alkyl mercaptyl, carboalkyl or carbamoyl. The preferred aralkyl groups are benzyl or phenethyl.

"Alkyl carbamoyl" means a carbamoyl group substituted by one or two alkyl groups. Preferred groups are the lower alkyl carbamoyl groups.

"Hydroxyalkyl" means an alkyl group substituted by a hydroxy group. Hydroxy lower alkyl groups are preferred. Exemplary preferred groups include hydroxymethyl, 2-hydroxyethyl, 2-hydroxypropyl, and 3-hydroxypropyl.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Alkoxyalkyl" means an alkyl group as previously described substituted by an alkoxy group as previously described.

"Aminoalkylene" means a group of the formula —$(CH_2)_n$—$NH_2$ where n is 1 to about 6. The preferred groups are the lower alkylene amino groups wherein lower alkylene groups are of 1 to about 4 carbon atoms. The most preferred amino alkylene group is aminomethylene.

Certain of the compounds of the present invention may exist in enolic or tautomeric forms, and all of these forms are considered to be included within the scope of this invention.

The compounds of this invention may be useful in the form of the free base, in the form of salts and as a hydrate. All forms are within the scope of the invention. Acid addition salts may be formed and are simply a more convenient form for use; and in practice, use of the salt form inherently amounts to use of the base form. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial cardiotonic properties inherent in the free base are not vitiated by side effects ascribable to the anions. Although pharmaceutically acceptable salts of said basic compound are preferred, all acid addition salts are useful as sources of the free base form even if the particular salt per se is desired only as an intermediate product as, for example, when the salt is formed only for purposes of purification and identification, or when it is used as an intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesulfonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

A preferred class of cardiotonic compounds of this invention is described by Formula I wherein the bicyclic ring of the molecule is represented by Formulae IIa-IIc, IIIa-IIIc or IVa-IVc, presented below:

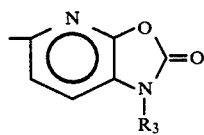

IIa

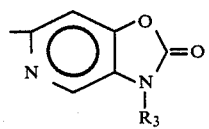

IIb

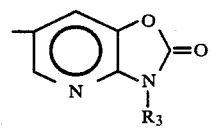

IIc

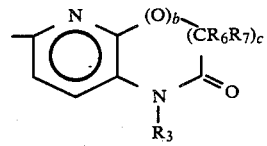

IIIa

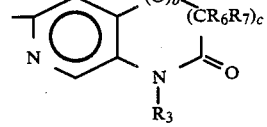

IIIb

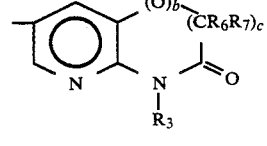

IIIc

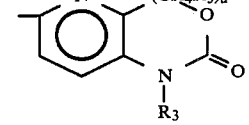

IVa

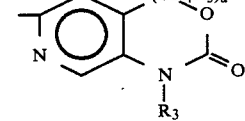

IVb

IVc wherein:

$R_3$, $R_4$, $R_5$, $R_6$ and $R_7$ are as described above and a and c are 1 or 2.

A more preferred class of compounds are of Formula I-IV above, wherein R is cyano, $R_2$ is lower alkyl and $R_1$, $R_3$, $R_4$, $R_5$, $R_6$, $R_7$ are hydrogen or lower alkyl.

Most preferred compounds are those disclosed by Formula I, wherein R is cyano, $R_1$ is hydrogen, $R_2$ is methyl and $R_3$ through $R_7$ are hydrogen or methyl.

A special embodiment of the invention comprises compounds of Formula IIIc where b+c add up to 2.

A further special embodiment comprises compounds of Formula I where $R_6$ and $R_7$ form a spiro ring system, two examples of which are shown by Formula V and Va below:

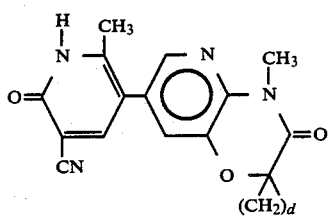

V

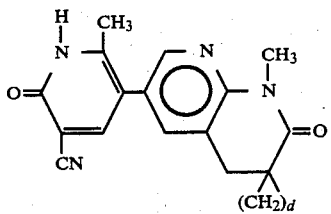

Va

Compounds of this invention may be prepared by constructing the pyridone ring substituent on the bicyclic portion of the compound as shown below in Scheme I.

or aralkylation of the lactam nitrogen with an appropriate alkylating agent results in the adduct of Formula VIII, which is oxopropylated by treatment with an acylated isopropenyl reagent and catalyst. A preferred catalytic system comprises the use of tri-o-tolylphosphine, palladium acetate, and tributyltin methoxide. Preferred reaction conditions comprise using a nonpolar solvent such as benzene and heating the reaction to a temperature which results in the preparation of the product in a reasonably short period of time of about 10 minutes to about two days. A preferred temperature range is about 75° to about 80° C. Condensation of the compound of Formula IX with N,N-dimethylformamide dimethylacetal results in the alpha, beta unsaturated keto-compound X. Cyclization to the compound of Formula Ia is accomplished by treatment with an appropriate amido-containing nucleophile which adds 1,2 to the unsaturated ketone and condenses with the ketone eliminating dimethylamine and water. A preferred nucleophile is sodium cyanoacetamide which may be prepared by the reaction of sodium hydride with cyanoacetamide or sodium ethoxide in ethanol. Compound X may also be condensed with nitroacetamide resulting in the compound of Formula I where R

SCHEME I

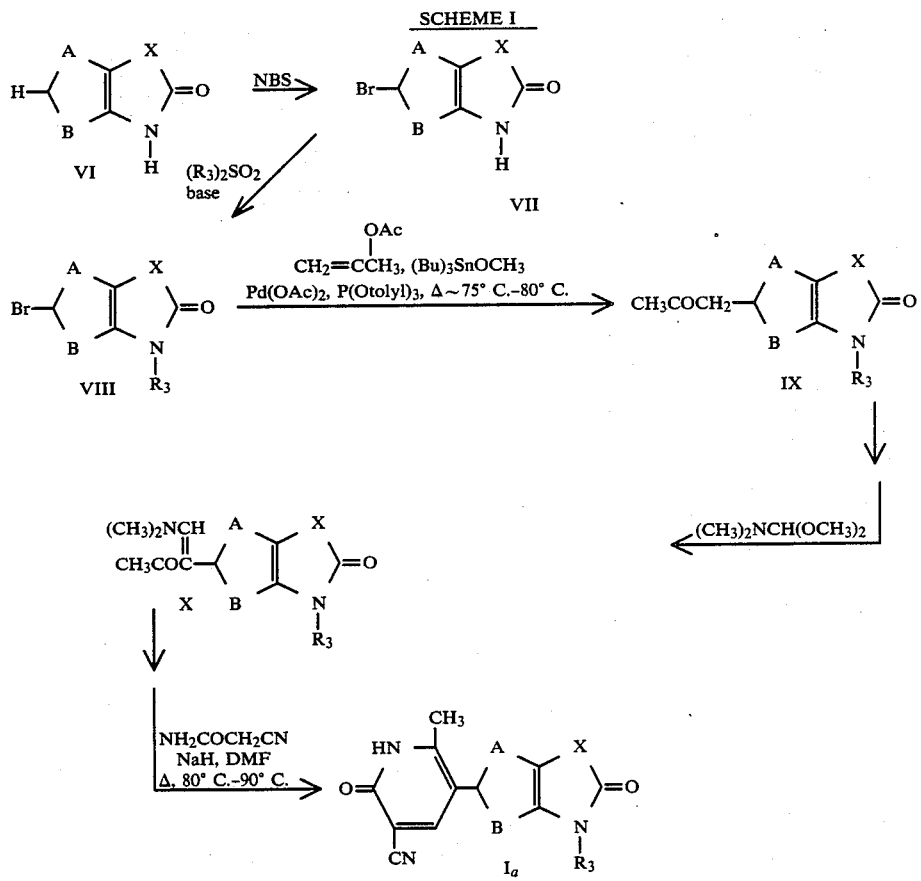

Halogenation of a compound of Formula VI results in the corresponding halogentated product VII. Bromination is a preferred reaction which occurs on the pyrido ring of the bicyclic compound in the position para to the nitrogen of the lactam. Bromination can be carried out with bromination reagents known in the art. A preferred method is N-bromosuccinimide in a polar, non-protic solvent such as DMF. Subsequent alkylation is $NO_2$. The cyclization reaction is conducted preferably at elevated temperature such as 70° to about 90° C., under inert conditions in a polar medium such as DMF or ethanol.

The cyano substituent in Formula Ia may be converted to other substituents defined for R in Formula I. For example the cyano group may be hydrolyzed to the acid which in turn can be esterified or converted to the amide. The ester may be converted by known methods to formyl which in turn can be reduced to the alkyl or hydroxyalkyl substituent. The alkoxyalkyl may be formed from the hydroxyalkyl.

The nitro-containing compound may be reduced to the amino compound from which the hydroxy and halo substituted compounds may be formed. These methods and reaction conditions would vary, of course, depending on the desired substituent and the substituent present, and are known to one skilled in the art.

The starting materials useful for the preparation of the compounds of this invention are known, can be prepared by known methods or prepared in accordance with the reaction sequences described below. For compounds of Formula I wherein b is 1, the bicyclic portion of the compound may be prepared according to the following reaction sequences.

When 2-amino-3-hydroxypyridine is treated with sodium hydride followed by ring closure with a α-haloacetate ester of the formula

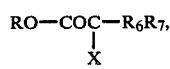

the pyridooxazinones are formed.

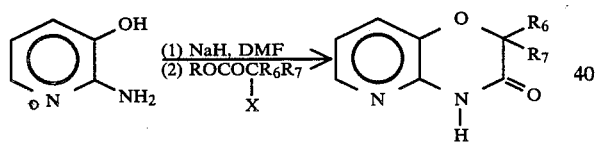

When the seven member-containing bicyclic ring is desired, the reaction is carried out using the halopropionate as show below.

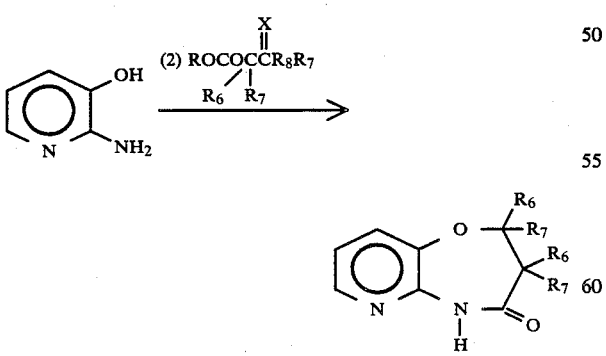

The five member-containing bicyclic ring is prepared by reacting 2-amino-3-hydroxypyridine with either phosgene or N,N-carbonyldiimidazole as shown below.

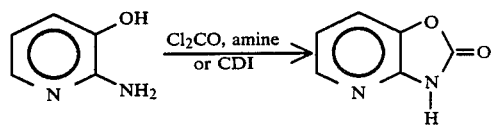

Those compounds where the oxygen atom of the pyrido-oxazinone ring is not directly on the pyridine ring are prepared from a 2-aminonicotinic acid or ester, reducing the latter to the corresponding alcohol and cyclizing as above.

These reactions are depicted in Schemes II and IIa below.

SCHEME II

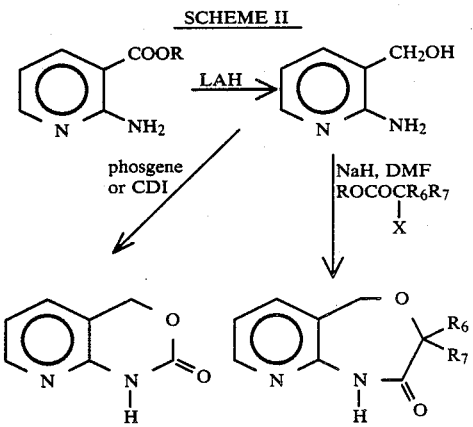

SCHEME IIa

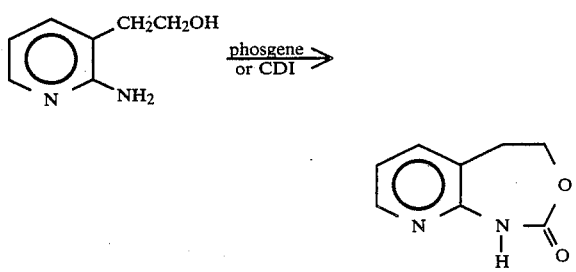

When the starting pyridine is 3-amino-4-hydroxypyridine or 2-hydroxy-3-aminopyridine then the corresponding pyridooxazinone is prepared as shown below.

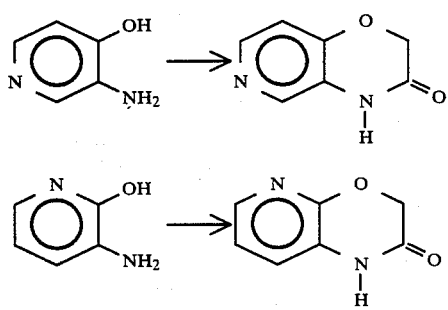

Compounds wherein $R_3$ is other than hydrogen are prepared from N-$R_3$-substituted amino-pyridines.

For compounds of Formula I wherein b is 0, the bicyclic portion of the compounds may be prepared according to one of the reaction sequences depicted in Scheme III below. Treatment of the 3-carbonyl-2-trimethylmethylamidopyridine compound depicted in Scheme III with a triphenylphosphine ylide reagent yields the unsaturated ylide addition product. The ylide chosen for the addition reaction may include $R_6$ and $R_7$ substituents other than hydrogen. Furthermore, the $R_8$ substituent on the ylide determines the size of the resultant saturated ring of the bicyclic end product as shown in Scheme III. Hydrogenation of the ylide addition product and acidic cylcization to the lactam provides the bicyclic system.

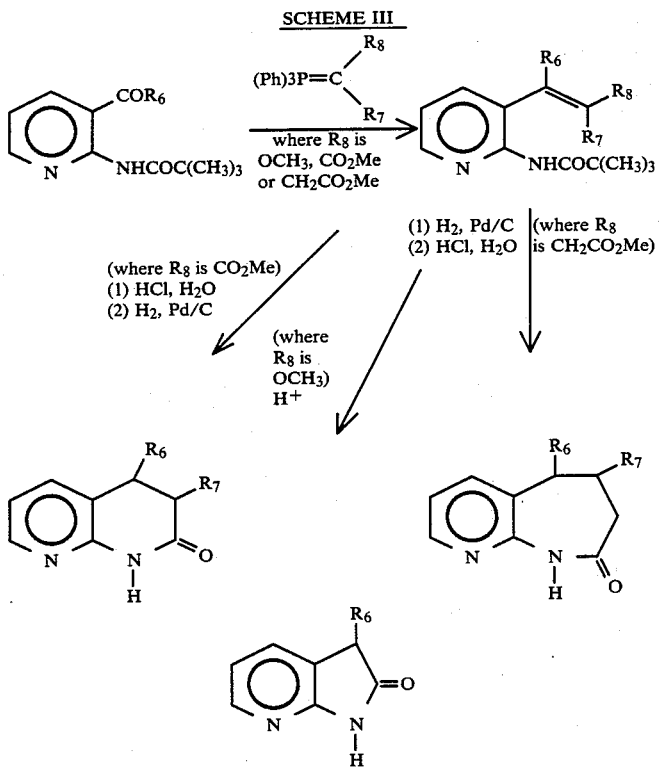

SCHEME III

N-alkylation and halogenation of the bicyclic ring proceeds in the same manner as described for the oxygen-containing bicyclic rings discussed above.

Introduction of a spiro group into the bicyclic rings wherein the carbon atom alpha to the lactam carbonyl is unsubstituted is accomplished by reacting the intermediate compound of Formulae VIII with a strong base such as lithium diisopropyl amide and a suitable dibromoalkane such as 1,2-dibromoethane or 1,4-dibromobutane.

Specific examples of the preparation of compounds of this invention are described below.

EXAMPLE 1

THE PREPARATION OF 7-[3'-CYANO-6'-METHYL-2-OXO-(1H)PYRIDIN-5'-YL]-4-METHYL-2H-PYRIDO[3,2-b]-1,4-OXAZIN-3(4H)-ONE

Step 1. 7-Bromo-2H-pyrido[3,2-b]-1,4-oxazin-3(4H)-one

To a solution of 5.6 g 2H-pyrido[3,2-b]-1,4-oxazin-3-(4H)-one dissolved in 85 ml of DMF under nitrogen is added 7.96 g NBS in 50 ml of DMF. This is allowed to stir at room temperature overnight. To this is added 35 ml of water and chilled. The solid material which separates is filtered and washed with $3 \times 100$ ml $H_2O$. This is then dried in a vac oven at 70° C. and then used directly in the next step.

Step 2.
4-Methyl-7-bromo-2H-pyrido[3,2-b]-1,4-oxazin-3(4H)-one

To a suspension of 5 g of 7-bromo-2H-pyrido[3,2-b]-1,4-oxazin-3(4H)-one (0.022 mole) in 90 ml of THF is added 24 ml of LiN(TMS)$_2$ (0.024 mole) in THF. The homogenous solution is maintained under nitrogen at room temperature for 20 min., 3.03 g (0.024 mole) of dimethylsulfate is added and the reaction mixture allowed to stir overnight. The reaction mixture is then quenched with 20 ml of sat. ammonium chloride and extracted with $3 \times 80$ ml ethyl acetate. The ethyl acetate is then washed with $3 \times 30$ ml sat. ammonium chloride, dried over sodium sulfate and concentrated to obtain off white product which is used directly in the next step.

Step 3.
4-Methyl-7-(2'-oxopropyl)-2H-pyrido[3,2-b]-1,4-oxazin-3(4H)-one

4-Methyl-7-bromo-2H-pyrido[3,2-b]-1,4-oxazin-3(4H)-one (3 g) (0.012 mole) in 80 ml of benzene is treated with 365 mg tri-o-tolylphosphine, 138 mg palladium acetate, 1.87 g (0.018 mole) of isopropenyl acetate and 5.9 g (0.18 mole) of tributyltin methoxide. The mixture is heated to 70° C. for 25 hours. The reaction mixture is then quenched with 20 ml sat. ammonium chloride and diluted with 50 ml ethyl acetate. The organic phase separates, dried over sodium sulfate and concentrated to dryness. The residue is dissolved in methylene chloride, washed with sat. KF solution, filtered through a cotton plug, dried over sodium sulfate and concentrated to dryness to obtain crude product. This is chromatographed using 200×60 mm $SiO_2$,EtOAc (100%) as eluent. The desired product is identified by NMR and used directly in the next step.

Step 4.
4-Methyl-7-[1'-N,N-dimethylamino-3'-oxobuten-2'-yl]-2H-pyrido[3,2-b]-1,4-oxazin-3(4H)-one To 1.05 g (0.0047 mole) of 4-methyl-7-(2'-oxopropyl)-2H-pyrido[3,2-b]-1,4-oxazin-3(4H)-one suspended in 10 ml of dimethylformamide dimethylacetal is added 1 ml of pyridine. This is then heated under nitrogen at 70° C. for 5 hours. The reaction mixture is then concentrated in vacuo to leave an dark oily solid. Trituration with methylene chloride gives a pale yellow solid which is filtered off and identified to be desired product by NMR. This is then used directly in the next step.

Step 5.
7-[3'-Cyano-6'-methyl-2'-oxo-(1H)pyridin-5'-yl]-4-methyl-2H-pyrido(3,2-b]-1,4-oxazin-3(4H)-one Sodium hydride (87 mg/oil) is washed with pet. ether and suspended in 4 ml of DMF under nitrogen. To this is added 166 mg of cyanoacetamide in 3 ml of DMF and the mixture stirred for about 5 min. A solution of 500 mg of 4-methyl-7-[1'-N,N-dimethylamino-3'-oxobuten-2'-yl]-2H-pyrido[3,2-b]-1,4-oxazin-3(4H)-one in 4 ml of DMF is added to the mixture and heated under nitrogen at 80° C. for 4.5 hours. This is then diluted with 15 ml of sat. ammonium chloride and extracted with 4×40 ml of ethyl acetate, dried over sodium sulfate and concentrated in vacuo. (M.P. 350° C.)

Calc'd. C, 59.36; H, 4.25; N, 18.46.
Found C, 59.44; H, 4.32; N, 18.56.

EXAMPLE 2

When 2H-pyrido[3,2-b]-1,4-oxazin-3-(4H)-one of Example 1, Step 1 is replaced with the compounds of Table I below, then the corresponding product is obtained.

Table I 2H-pyrido[3,2-b]-1,4-oxazin-3(4H)-one
2H-pyrido[4,3-b]-1,4-oxazin-3(4H)-one
2H-pyrido[2,3-b]-1,4-oxazin-3(4H)-one
4H-pyrido[2,3-d][1,3]oxazin-2(1H)-one
4H-pyrido[3,4-d][1,3]oxazin-2(1H)-one
4H-pyrido[3,2-d][1,3]oxazin-2(1H)-one
oxazolo[4,5-b]pyridin-2(3H)-one
oxazolo[4,5-c]pyridin-2(3H)-one
oxazolo[5,4-b]pyridin-2(3H)-one
2,3-dihydropyrido[3,2-b][1,4]oxazepin-4(5H)-one
2,3-dihydropyrido[4,3-b][1,4]oxazepin-4(5H)-one
2,3-dihydropyrido[2,3-b][1,4]oxazepin-4(5H)-one
3,5-dihydropyrido[2,3-e]-1,4-oxazepin-2-(1H)-one
3,5-dihydropyrido[3,4-e]-1,4-oxazepin-2-(1H)-one
3,5-dihydropyrido[3,2-e]-1,4-oxazepin-2-(1H)-one
4,5-dihydropyrido[2,3-d]-1,3-oxazepin-2(1H)-one
4,5-dihydropyrido[3,4-d]-1,3-oxazepin-2(IH)-one
4,5-dihydropyrido[3,2-d]-1,3-oxazepin-2(1H)-one

EXAMPLE 3

The Preparation of 6-[3'-Nitro-6'-Methyl-2-Oxo-(1H)Pyridin-5'-YL]-3-Methyl-Oxazolo[4,5-b]Pyridin-2(3H)-One

Step 1. 6-Bromo-oxazolo[4,5-b]pyridin-2(3H)-one

To a solution of 5.07 g oxazolo[4,5-b]pyridin-2(3H)-one dissolved in 85 ml of DMF under nitrogen is added 7.46 g NBS in 50 ml of DMF. This is allowed to stir at room temperature overnight. To this is added 35 ml of water and chilled. The solid material which separates is filtered and washed with 3×100 ml $H_2O$. This is then dried in a vac oven at 70° C. and then used directly in the next step.

Step 2.
3-Methyl-6-bromo-oxazolo[4,5-b]pyridin-2(3H)-one

To a suspension of 4.7 g of 6-bromo-oxazolo[4,5-b]pyridin-2(3H)-one (0.022 mole) in 90 ml of THF is added 24 ml of $LiN(TMS)_2$ (0.024 mole) in THF. The homogenous solution is maintained under nitrogen at room temperature for 20 min., 3.03 g (0.024 mole) of dimethylsulfate is added and the reaction mixture allowed to stir overnight. The reaction mixture is then quenched with 20 ml of sat. ammonium chloride and extracted with 3×80 ml ethyl acetate. The ethyl acetate is then washed with 3×30 ml sat. ammonium chloride, dried over sodium sulfate and concentrated to obtain off white product which is used directly in the next step.

Step 3.
3-Methyl-6-(2'-oxopropyl)oxazolo[4.5-b]pyridin-2-(3H)-one

3-Methyl-6-bromo-oxazolo[4,5-b]pyridin-2(3H)-one (2.58 g) (0.012 mole) in 80 ml of benzene is treated with 365 mg tri-o-tolylphosphine, 138 mg palladium acetate, 1.87 g (0.018 mole) of isopropenyl acetate and 5.9 g (0.18 mole) of tributyltin methoxide. This is sealed in a high pressure tube and heated to 70° C. for 25 hours. The reaction mixture is then quenched with 20 ml sat. ammonium chloride and diluted with 50 ml ethyl acetate. The organic phase separates, dried over sodium sulfate and concentrated to dryness. The residue is dissolved in methylene chloride, washed with sat. KF solution, filtered through a cotton plug, dried over sodium sulfate and concentrated to dryness to obtain crude product. This is chromatographed using 200×60 mm $SiO_2$, EtOAc (100%) as eluent. The desired product is identified by NMR and used directly in the next step.

Step 4.
3-Methyl-6-[1'-N,N-dimethylamino-3'-oxobuten-2'-yl]-oxazolo(4,5-b)pyridin-2(3H)-one To 1.47 g (0.007 mole) of 3-methyl-6-(2'-oxopropyl)oxazolo[4,5-b]pyridin-2(3H)-one suspended in 15 ml of dimethylformamide dimethylacetal is added 1.5 ml of pyridine. This is then heated under nitrogen at 70° C. for 5 hours. The reaction mixture is then concentrated in vacuo to leave a dark oily solid. Trituration with methylene chloride gives a solid which is filtered off and identified to be desired product by NMR. This is then used directly in the next step.

Step. 5.
6-[3'-Nitro-6'-methyl-2'-oxo-(1H)pyridin-5'-yl]-3-methyl-oxazolo[4,5-b]pyridin-2(3H)-one Sodium hydride (174 mg/oil) is washed with pet. ether and suspended in 10 ml of DMF under nitrogen. To this is added 330 mg of nitroacetamide in 6 ml of DMF and the mixture stirred for about 5 min. A solution of 940 mg of 3-methyl-6-[1'-N,N-dimethylamino-3'-oxobuten-2'-yl]-oxazolo[4,5-b]pyridin-2(3H)-one in 10 ml of DMF is added to the mixture and heated under nitrogen at 80° C. for 4.5 hours. This is then diluted with 30 ml of sat. ammonium chloride and extracted with 4×75 ml of ethyl acetate, dried over sodium sulfate and concentrated in vacuo.

EXAMPLE 4

When nitroacetamide is replaced in Example 3, Step 5 by cyanoacetamide then the product prepared is 6-[3'-cyano-6'-methyl-2'-oxo-(1H)pyridin-5'-yl]-3-methyl-oxazolo[4,5-b]pyridin-2(3H)-one.

EXAMPLE 5

When dimethylsulfate is replaced in Examples 1 and 3, Step 2, with benzylbromide, then 4-benzyl-7-bromo-2H-pyrido[3,2-b]-1,4-oxazin-3(4H)-one and 3-benzyl-6-bromo-oxazolo[4,5-b]pyridin-2(3H)-one are produced.

EXAMPLE 6

Following the procedures of Examples 1-5, the following compounds may be prepared:
7-[3'-cyano-6'-methyl-2'-oxo-(1H)pyridin-5'-yl]-4-methyl-2H-pyrido[4,3-b]-1,4-oxazin-3(4H)-one.
7-[3'-cyano-6'-methyl-2'-oxo-(1H)pyridin-5'-yl]-4-methyl-2H-pyrido[2,3-b]-1,4-oxazin-3(4H)-one.
6-[3'-cyano-6'-methyl-2'-oxo-(1H)pyridin-5'-yl]-3-methyloxazolo[4,5-b]pyridin-2(3H)-one.
6-[3'-cyano-6'-methyl-2'-oxo-(1H)pyridin-5'-yl]-3-methyloxazolo[4,5-c]pyridin-2(3H)-one.
6-[3'-cyano-6'-methyl-2'-oxo-(1H)pyridin-5'-yl]-3-methyloxazolo[5,4-c]pyridin-2(3H)-one.
6-[3'-cyano-6'-methyl-2'-oxo-(1H)pyridin-5'-yl]-1-methyl-4H-pyrido[2,3-d][1,3]oxazin-2(1H)-one.
8-[3'-cyano-6'-methyl-2'-oxo-(1H)pyridin-5'-yl]-5-methyl-2,3-dihydropyrido[3,2-b][1,4]oxazepin-4(5H)-one.
8-[3'-cyano-6'-methyl-2'-oxo-(1H)pyridin-5'-yl]-5-methyl-2,3-dihydropyrido[4,3-b][1,4]oxazepin-4(5H)-one.
7-[3'-cyano-6'-methyl-2'-oxo-(1H)pyridin-5'-yl]-1-methyl-3,5-dihydropyridin[2,3-e]-1,4-oxazepin-4(1H)-one.
7-[3'-amino-6'-methyl-2'-oxo-(1H)pyridin-5'-yl]-4-methyl-2H-pyrido[3,2-b]-1,4-oxazin-3(4H)-one.
7-[3'-chloro-6'-methyl-2'-oxo-(1H)pyridin-5'-yl]-4-methyl-2H-pyrido[3,2-b]-1,4-oxazin-3(4H)-one.
7-[3'-methoxymethyl-6'-methyl-2'-oxo-(1H)pyridin-5'-yl]-4-methyl-2H-pyrido[3,2-b]-1,4-oxazin-3(4H)-one.
7-[3',6'-dimethyl-2'-oxo-(1H)pyridin-5'-yl]-4-methyl-H-pyrido[3,2-b]-1,4-oxazin-3(4H)-one.
7-[3'-cyano-6'-methyl-2'-oxo-(1H)pyridin-5'-yl]-benzyl-2H-pyrido[3,2-b]-1,4-oxazin-3(4H)-one.
7-[3'-cyano-6'-methyl-2'-oxo-(1H)pyridin-5'-yl]-4-ethyl-2H-pyrido[3,2-b]-1,4-oxazin-3(4H)-one.
7-[3'-cyano-6'-methyl-2'-oxo-(1H)pyridin-5'-yl]-2H-pyrido[3,2-b]-1,4-oxazin-3(4H)-one.
7-[3'-cyano-6'-methyl-2'-oxo-(1H)pyridin-5'-yl]-2,2,4-trimethyl-2H-pyrido[3,2-b]-1,4-oxazin-3(4H)-one. (M.P. >300° C.)

Calc'd. C, 61.93; H, 4.55; N, 18.06. Found C, 61.64; H, 4.95; N, 17.14. Confirmed by high resolution mass spec.
7-[3'-cyano-6'-methyl-2'-oxo-(1H)pyridin-5'-yl]-2-methyl-2H-pyrido[3,2-b]-1,4-oxazin-3(4H)-one. (M.P. >310° C.)
Calc'd. C, 62.95; H, 4.47; N, 17.27. Found C, 62.61; H, 5.18; N, 16.94.
7-[3'-cyano-6'-methyl-2'-oxo-(1H)pyridin-5'-yl]-2,4-dimethyl-2H-pyrido[3,2-b]-1,4-oxazin-3(4H)-one. (M.P. >300° C.)
Calc'd C, 61.04; H, 4.64; N, 17.79. Found C, 61.08; H, 4.72; N, 17.65. As the quarterhydrate
7-[3'-cyano-6'-methyl-2'-oxo-(1H)pyridin-5'-yl]-2-phenyl-2H-pyrido[3,2-b]-1,4-oxazin-3(4H)-one. (M.P. 224°–246° C.)
Calc'd. C, 66.92; H, 4.42; N. 14.87. Found C, 66.81; H, 4.84; N, 14.52. As the quarterhydrate

EXAMPLE 7

The Preparation of 6-[3'-Cyano-6'-Methyl-2'-Oxo-(1H)Pyridin-5'-YL]-3,4-Dihydro-1-Methyl-1,8-Naphtheridin-2(1H)-One

Step 1. 2-(Pivaloylamino)pyridine

A solution of pivaloyl chloride (96 g) in methylene chloride (200 ml) is added dropwise to a cooled mixture of 2-aminopyridine (50 g) and triethylamine (108 g) in methylene chloride (650 ml). The reaction mixture is stirred overnight at RT and poured into water which is basified and the organic layer separated and concentrated in vacuo. Hexane is added to the oil which results in the precipitation of a crystalline solid which is filtered and the solid taken up in aqueous acid. The desired pyridine compound is recrystallized as a white crystalline solid.

Step 2. 3-Formyl-2-(pivaloylamino)pyridine

N-Butyl lithium (112 ml) is added dropwise to a stirred solution of the pyridine prepared according to step 1 (20 g) in THF (250 ml) at −78° C. The reaction mixture is warmed to 0° C. for about 4 hours and cooled to −78° C. Dimethyl formamide (30 ml) is added to the cooled reaction mixture and the mixture stirred overnight at RT. The reaction mixture is quenched with sat'd aqueous NH₄Cl and diluted with ethyl acetate. The organic layer is separated, concentrated and treated with aqueous acid. The aqueous layer is washed with ethyl acetate, brought to a neutral pH and extracted with ethyl acetate. The organic extract is dried, concentrated in vacuo and cooled, resulting in the formation of a crystalline material which is further purified on a silica gel column to afford a white crystalline solid used in the next step.

Step 3. 3-(2-Carbomethoxyvinyl)-2-(pivaloylamino)-pyridine

A solution of the formyl compound of step 2. above (9.8 g) in methylene chloride (100 ml) is added dropwise to a solution of carbomethoxymethylide triphenylphosphine (16 g) in methylene chloride (125 ml). The reaction mixture is stirred at reflux overnight, cooled to RT, concentrated in vacuo and petroleum ether added. The ethereal solution is cooled resulting in the precipitation of the desired material as a white crystalline solid, M.P 148°–150° C. Step 4. 3,4-Dihydro-1,8-naphtheridin-2(1H)-one A solution of the carbomethoxy vinyl compound of step 3. above (9 g), 10% Pd on C in ethanol (400 ml) is introduced into a Parr apparatus and stirred under hydrogen until the reaction is complete. The reaction mixture is filtered, the filtrate concentrated in vacuo, and the residue dissolved in 6N HCl and stirred at 110° C. overnight. The reaction mixture is neutralized, extracted with chloroform and dried, filtered and concentrated in vacuo. The resulting solid is chromatographed on silica gel resulting in a purified white crystalline product, M.P. 160°–162° C.

Step 5.
6-Bromo-3,4-dihydro-1,8-naphtheridin-2(1H)-one

A solution of N-bromosuccinimide (3.7 g) in dimethyl formamide (70 ml) is added dropwise to a stirring solution of the naphtheridine of step 4. above maintained at about −10° C. The reaction mixture is warmed to RT and stirred overnight. Water is added to the mixture and the resulting suspension is stirred for 15 min., filtered, the filtered solid washed with water and recrystallized from DMF to yield the desired product as a white crystalline solid.

Step 6.
6-Bromo-3,4-dihydro-1-methyl-1,8-naphtheridin-2(1H)-one

A 1M solution of lithium bistrimethylsilylamide in THF (6.6 ml) is added dropwise to a stirring solution of the bromide from step 5 above (1.2 g) in THF (100 ml) at 0° C. The mixture is allowed to warm to RT and stirred for about 1 hour. Dimethyl sulfate (0.8g) is added to the mixture which is stirred for about 2 hours. The reaction is quenched with sat'd aqueous NH4Cl and the organic layer is separated, washed with sat'd NH4Cl solution, concentrated in vacuo, and the residue taken up in chloroform. The chloroform solution is washed with water, dried, concentrated and chromatographed on silica gel to yield the desired product as a clear white crystalline solid, M.P.=78°–80° C.

Step 7.
6-(2-oxopropyl)-3,4-dihydro-1-methyl-1,8-naphtheridin-2(1H)-one

Para-triorthotolylphosphine (0.1 g), palladium acetate (0.05 g), 2-acetoxypropene (0.6 g) and tributyltin methoxide (2g) are added to a solution of the bromide from step 6 above (1 g) in benzene (40 ml), and the resulting reaction mixture is stirred under $N_2$ at 80° C. for about 2.5 hours. The mixture is filtered, concentrated in vacuo, and the residue taken up in acetonitrile. The solution is filtered and the filtrate washed with hexanes. The acetonitrile layer is dried, filtered and concentrated in vacuo yielding the desired product as a crystalline solid, M.P.=93°–95° C.

Step 8.
6-(1-N,N'-Dimethylamino-3-oxobuten-2-yl)-2-oxopropyl)-3,4-dihydro-1-methyl-1,8-naphtheridin-2(1H)-one Dimethylformamide dimethylacetal (4.6 ml) is added to a solution of the compound of step 7. above (0.7 g) in methylene chloride (25 ml) and the reaction mixture stirred under nitrogen overnight. The mixture was evaporated yielding the desired product as an oil which is used as is in the next step.

Step 9.
6-[3'-Cyano-6'-methyl-2'-oxo-(1H)pyridin-5'-yl]-3,4-dihydro-1-methyl-1,8-naphtheridin-2(1H)-one A solution of the dimethylamino enamine of step 8 above (0.7 g) in absolute ethanol (45 ml) is added to a mixture prepared by adding a 21% solution of sodium methoxide in ethanol(1.5 ml) to a solution of cyanoacetamide (0.3 g) in ethanol (25ml). The reaction mixture is stirred at reflux under nitrogen overnight. The mixture is cooled to RT, concentrated in vacuo, and chromatographed on silica gel. The fractions including the solid desired product are recrystallized twice from isopropyl alcohol affording the desired product as a crystalline material, M.P.=230° C. (dec).

Calc'd. C, 63.73; H, 4.94; N, 18.58. Found C, 63.84; H, 4.94; N, 18.30.

The compounds of Formula I possess positive inotropic activity and are useful as cardiotonic agents in the treatment of humans and other mammals for cardiac disorders including congestive heart failure. The effectiveness of the compounds of this invention a inotropic agents may be determined by the following pharmacologic tests which evaluate the change in cardiac contractile force upon exposure to a dose of said compounds. The ganglionic-beta blocked anesthetized dog procedure is one such standard test procedure; the inotropic results of this procedure generally correlate with the inotropic activity found in human patients.

Ganglionic-Beta Blocked Anesthetized Dog Procedure

Adult mongrel dogs of either sex weighing 10 to 16 kg are fasted overnight, anesthetized with pentobarbital sodium 35 mg/kg, i.v. intubated, respired with room air using a Harvard respirator, and instrumented surgically to monitor myocardial contractile force, heart rate, arterial pressure, aortic flow and EKG limb lead II. The aforesaid measurements are recorded continuously on a strip chart recorder.

Myocardial contractile force is monitored by a Walton-Brodie strain gauge sutured to the left ventricular myocardium parallel to the left anterior descending coronary artery. Arterial pressure is measured using a fluid-filled catheter attached to a pressure transducer introduced via the right femoral artery and positioned in the thoracic aorta. Mean arterial pressure is determined by electronically clamping the pulsatile pressure signal. Aortic flow is monitored using a precalibrated, noncanulating electromagnetic flow probe positioned around the thoracic aorta. Heart rate is monitored using a cardiotachometer triggered by the QRS complex of the limb lead II EKG. The right femoral vein is cannulated for intravenous infusion of drugs. Body temperature is maintained at 37° C.

Following a 30 min postsurgical stabilization period, control valves are recorded. Myocardial depression is induced by ganglionic and beta receptor blockade. Initially, the responsiveness of the autonomic nervous systems is assessed by performing a 30 sec bilateral carotid occlusion (BCO). Ten minutes later, a saline solution of isoproterenol 0.3 mg/kg, i.v. is administered to assess beta receptor integrity. Ten minutes after that, a saline solution of mecamylamine 2 mg/kg, i.v. is infused, followed by a saline solution of propranolol 1 mg/kg, i.v. plus 0.3 mg/kg/hr. Twenty minutes later, a second BCO is performed to demonstrate ganglionic blockade followed by a second injection of saline isoproterenol 0.3 mg/kg, i.v. to demonstrate beta blockade. Ten minutes later, the test compound or vehicle is administered intravenously in ascending doses at 30 min intervals at 1.5 ml/min in a total volume of 3.5 ml. On completion of the experiment, both BCO and isoproterenol challenges are repeated to verify ganglionic and beta blockade.

The results of the blocked dog test show that compounds of the present invention increase contractile force and heart rate, and aortic blood flow in a dose related manner while maintaining arterial pressure.

Additional test procedures which have been found to be an efficient means for ascertaining the inotropic activity of the compounds of this invention are described below.

Guinea Pig Atria Inotropic Screening Concentrations

Guinea pigs are stunned by a sudden blow to the head; their chests are opened and hearts excised and placed in Kreb $\propto$ s medium (concentrations, mM: NaCl, 118.39; KCl, 4.70; MgSO$_4$, 1.18; KH$_2$PO$_4$, 1.18; NaHCO$_3$, 25.00; glucose, 11.66 and CaCl$_2$, 1.25 gassed with a mixture of 95% O$_2$. Left atria are removed and inserted into warmed (33° C.) double jacketed tissue chambers containing oxygenated Kreb's medium (as above). The upper end of each tissue is attached to a Statham Universal Transducing Cell via a Statham Microscale Accessory. Resting tension on each tissue is set at 1 g and adjusted periodically.

Massive field stimulation is achieved via a pair of platinum or silver electrodes placed on opposite sides of the tissue. Electrodes are made from 2-gauge silver wire wound into a tight coil approximately 12-14 mm in diameter. Electrodes are connected to a Grass stimulator via Grass constant current unit. Tissues are driven at 90 pulses per minute with 5 msec duration at current levels 20% greater than threshold for continuous beat.

Cumulative concentrations of test drugs are added to the tissue bath at intervals sufficient to allow developed tension to peak at a new level.

The increase in developed tension is each tissue for each compound concentration is measured, and the results are averaged and used to construct cumulative concentration-response curves. Slopes for these regressions calculated via the method of Finney (1971) are compared using Student's t-test.

The following in vitro method is another means for measuring the inotropic potency of the present compounds. This method is a modification of the enzyme inhibition method reported by Thompson and Appleman (1970) and Thompson et al. (1974), and is believed to correlate to in vivo inotropic activity in humans.

Inhibition of Peak III cAMP Phosphodiesterase Activity

The test compounds are included in media comprising a radioactivity labeled substrate ($^3$H-cyclic nucleotide) such as adenosine 3':5'-monophosphate (cyclic AMP) and quanine-3':5'-nucleotidease isolate from a dog heart. The inhibition of the enzyme hydrolysis of the 5'-nucleotide product of the cNUC-PDEase to the corresponding nucleoside is measured by separating the charged, unhydrolyzed substrate from the uncharged hydrolysis product. Separation may be achieved either chromatographically from the uncharged nucleoside product of the assay with ion exchange resin so that it is not quantitated with the liquid scintillation counter.

Anesthetized Dog Procedure

Male mongrel dogs are anesthetized with pentobarbital (35 mg/kg, i.v.) and intubated. Femoral artery and veins are cannulated for measurement of blood pressure and injection of compounds, respectively. A catheter connected to a Statham transducer is inserted into the left ventricle via the right carotid artery for measurement of left ventricular pressure, left ventricular end diastolic pressure and dP/dt. Lead II ECG and heart rate are also monitored. All parameters are measured on a Beckman Dynagraph.

Two additional test procedures which have been found to be an efficient means for ascertaining the inotropic activity of the compounds of this invention are described below.

Conscious Instrumented Dog

Female mongrel dogs (18.0–18.5 kg) are anesthetized with sodium pentobarbital (35 mg/kg, i.v., supplemented as necessary during surgery) intubated and connected to a Harvard respirator. The left side of the chest is opened at the fifth intercostal space, and a Konigsberg transducer inserted into the left ventricle through a puncture at the apex and secured. A fluid-filled polyethylene catheter is inserted into the left atrium through a puncture wound and secured for measurement of left atrial pressure. A second fluid-filled catheter is inserted into the aorta for measurement of blood pressure and heart rate and secured to the vessel wall. The two catheters and the Konigsberg transducer cable are passed out of the chest through the seventh intercostal space and advanced subcutaneously to the back of the neck and passed through the skin. The fluid-filled catheters are filled with heparinized 50% dextrose solution, and the chest is closed and evacuated.

The dog is trained and acclimated to its environment and the presence of personnel during the experiment.

The dogs are fasted overnight before either intravenous or oral administration of the compound. On a test day, the dog is placed in a sling and connected to a recorder (Gould Instruments or Grass Instruments) for measurement of left ventricular pressure, left ventricular dP/dt$_{max}$, blood pressure, heart rate (from the blood pressure signal), and the lead II electrocardiogram. The compound is administered both intravenously and orally (liquid and soft gelatin capsule forms) in different experiments and blood samples were taken for determination of blood levels of the compound.

The compounds of this invention can be normally administered orally or parenterally, in the treatment of cardiac disorders such as heart failure in humans or other mammals.

The compounds of this invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of inotropic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegratants such as starch, alginic acid and certain complex silicates, together with lubricating agents such as magnesium stearate, sodium lauryl; sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, also useful for intravenous injection purposes, provided that their pH is properly adjusted, suitably buffered, made isotonic with sufficient saline or glucose and sterilized by heating or by microfiltration.

The dosage regimen in carrying out the methods of this invention is that which insures maximum therapeutic response until improvement is obtained and thereafter the minimum effective level which gives relief. Thus, in general, the dosages are those that are therapeutically effective in increasing the contractile force of the heart or in the treatment of cardiac failure. In general, the oral dose may be between about 0.01 mg/kg and about 50 mg/kg (preferably in the range of 0.1 to 10 mg/kg), and the i.v. dose about 0.005 to about 30 mg/kg (preferably in the range of 0.01 to 3 mg/kg), bearing in mind, of course, that in selecting the appropriate dosage in any specific case, consideration must be given to the patient's weight, general health, age and other factors which may influence response to the drug. The drug may be administered as frequently as is necessary to achieve and sustain the desired therapeutic response. Some patients may respond quickly to a relatively large or small dose and require little or no maintenance dosage. On the other hand, other patients may require sustained dosing from about 1 to about 4 times a day depending on the physiological needs of the particular patient. Usually the drug may be administered orally 1 to 4 times per day. It is anticipated that many patients will require no more than about one to about two doses daily.

It is also anticipated that the present invention would be useful as an injectable dosage form which may be administered in an emergency to a patient suffering from acute cardiac failure. Such treatment may be followed by intravenous infusion of the active compound and the amount of compound infused into such a patient should be effective to achieve and maintain the desired therapeutic response.

We claim:

1. A compound of the formula

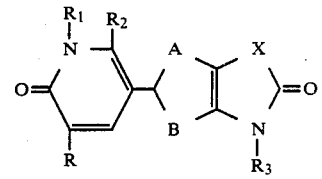

wherein:
A is —C= or —N=;
B is —C=C—; —C=N— or —N=C—;
provided that A or B represents a nitrogen-containing group;
X is —(CR$_4$R$_5$)$_a$—(O)$_b$—(CR$_6$R$_7$)$_c$—;
a and c are 0, 1 or 2;
b is 0 or 1;
provided that a+b+c=1
R is hydrogen, alkyl, alkoxyalkyl, hydroxyalkyl, nitro, halo, cyano, carbamoyl, alkyl carbamoyl, formyl, aminoalkylene or amino;
R$_1$, R$_2$, R$_3$, R$_5$, R$_6$ and R$_7$ are hydrogen, alkyl, or aralkyl;
R$_4$ is hydrogen, alkyl, aryl, or aralkyl;
geminal R$_6$ and R$_7$ groups may together form a spiro substituent, —(CH$_2$)$_d$—, where d is 2 to 5;
or a pharmaceutically acceptable salt thereof.

2. A compound according to claim 1 where R is cyano, R$_2$ is lower alkyl and R$_1$, R$_3$, R$_4$, R$_5$, R$_6$ and R$_7$ are hydrogen or lower alkyl.

3. A compound according to claim 2 where
R is cyano;
R$_1$ is hydrogen;
R$_2$ is methyl; and
R$_3$, R$_4$, R$_5$, R$_6$, and R$_7$ are hydrogen or methyl.

4. A compound according to claim 3 where
A is —C=;
B is —C=N—; and
X is —O—.

5. A compound according to claim 1 where b is 0.

6. A compound according to claim 5 where
A is —C=; and
B is —C=N—.

7. A compound according to claim 6 wherein a+c equals 1.

8. A compound according to claim 7 wherein c is 1 and geminal R$_6$ and R$_7$ groups together form a spiro substituent.

9. A compound according to claim 1 which is 6-[3'-cyano-6'-methyl-2'-oxo-(1H)pyridin-5'-yl]-3-methyloxazolo-[4,5-b]pyridin-2(3H)-one or a pharmaceutically acceptable salt thereof.

10. A method for increasing cardiotonic contractility in a patient requiring such treatment which comprises administering to such patient an effective amount of a compound according to claim 1.

11. A pharmaceutical composition wherein the active ingredient is a compound according to claim 1 in admixture with a pharmaceutical carrier.

* * * * *